US012433927B2

(12) United States Patent
Mollick

(10) Patent No.: US 12,433,927 B2
(45) Date of Patent: *Oct. 7, 2025

(54) THERAPEUTIC TREATMENT FOR THE CORONAVIRUS DISEASE COVID-19

(71) Applicant: Peter Joseph Mollick, Phoenix, AZ (US)

(72) Inventor: Peter Joseph Mollick, Phoenix, AZ (US)

( * ) Notice: Subject to any disclaimer, the term of this patent is extended or adjusted under 35 U.S.C. 154(b) by 193 days.

This patent is subject to a terminal disclaimer.

(21) Appl. No.: 18/388,823

(22) Filed: Nov. 11, 2023

(65) Prior Publication Data

US 2024/0075090 A1 Mar. 7, 2024

Related U.S. Application Data

(62) Division of application No. 18/104,030, filed on Jan. 31, 2023, now Pat. No. 11,865,154, which is a division of application No. 17/602,234, filed as application No. PCT/US2021/025298 on Apr. 1, 2021, now abandoned.

(60) Provisional application No. 63/102,925, filed on Jul. 8, 2020, provisional application No. 63/100,831, filed on Apr. 2, 2020.

(51) Int. Cl.

| | |
|---|---|
| ***A61K 36/00*** | (2006.01) |
| ***A61K 9/48*** | (2006.01) |
| ***A61K 36/53*** | (2006.01) |

(52) U.S. Cl.

CPC ............ *A61K 36/53* (2013.01); *A61K 9/4833* (2013.01)

(58) Field of Classification Search

CPC ................................ A61K 9/4833; A61K 9/20
See application file for complete search history.

(56) References Cited

U.S. PATENT DOCUMENTS

| | | | |
|---|---|---|---|
| 2004/0071757 | A1 | 4/2004 | Rolf |
| 2006/0270614 | A1 | 11/2006 | Boddupalli et al. |
| 2015/0258287 | A1 | 9/2015 | Shahaf et al. |
| 2017/0157190 | A1 | 6/2017 | Lamb et al. |
| 2022/0143121 | A1 | 5/2022 | Mollick |
| 2023/0173010 | A1 | 6/2023 | Mollick |

OTHER PUBLICATIONS

Case Adams Thyme Antiviral Against Herpes and Other Viruses the Journal of Plant Medicines Oct. 3, 2017 https ://plantmedicines. org/thyme-provides-anti viral-protection-against-herpes-and-other-viruses/.

*Primary Examiner* — Qiuwen Mi

(57) ABSTRACT

A therapeutic treatment for the treatment of COVID-19 disease, the treatment to be initiated soon after and preferably within approximately twenty four hours after a patient develops the first signs of symptoms comprising but not limited to individually or in combination thereof fever, headache, sore joints, cough, fatigue, chills. The treatment consists of the oral administration of an herb thyme also know as common thyme (*Thymus Vulgaris*). The treatment is thought to inhibit the replication and activity of the virus allowing the patient to regain normal health and assist in developing immunity to the virus. The treatment is not known to completely eliminate the virus from the patient therefore resulting in the patient possibly developing the same or different symptoms of the disease a second, or more times requiring additional treatments of the disclosed thyme therapeutic treatment.

15 Claims, No Drawings

THERAPEUTIC TREATMENT FOR THE CORONAVIRUS DISEASE COVID-19

CROSS-REFERENCE TO RELATED APPLICATIONS

This application claims priority to and is a Divisional Application of U.S. patent application Ser. No. 18/104,030 titled "Therapeutic Treatment for the Coronavirus Disease COVID-19" filed Jan. 31, 2023, which claims the benefit of U.S. patent application Ser. No. 17/602,234 titled "Therapeutic Treatment for the Coronavirus Disease COVID-19" filed Oct. 7, 2021, which claims the benefit of U.S. International PCT Application No. PCT/US2021/025298 filed Apr. 1, 2021, and also claims the benefit of U.S. Provisional Patent Application No. 63/102,925 titled "Medical Herbal Coronavirus Treatment" filed Jul. 8, 2020, and also claims the benefit of U.S. Provisional Patent Application No. 63/100,831 titled "Medical Herbal Treatment" filed Apr. 2, 2020, the contents of all applications which are incorporated herein by reference in their entirety.

BACKGROUND OF THE INVENTION

Information from Wikipedia on 2021-03-27 on pages 1 through 17.

Coronaviruses are a group of related RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause SARS, MERS, and COVID-19. In cows and pigs they cause diarrhea, while in mice they cause hepatitis and encephalomyelitis.

Coronaviruses constitute the subfamily Orthocoronavirinae, in the family Coronaviridae, order Nidovirales, and realm Riboviria. They are enveloped viruses with a positive-sense single-stranded RNA genome and a nucleocapsid of helical symmetry. The genome size of coronaviruses ranges from approximately 26 to 32 kilobases, one of the largest among RNA viruses. They have characteristic club-shaped spikes that project from their surface, which in electron micrographs create an image reminiscent of the solar corona, from which their name derives.

Etymology

The name "coronavirus" is derived from Latin corona, meaning "crown" or "wreath", itself a borrowing from Greek______kor_n_, "garland, wreath" The name was coined by June Almeida and David Tyrrell who first observed and studied human coronaviruses. The word was first used in print in 1968 by an informal group of virologists in the journal Nature to designate the new family of viruses. The name refers to the characteristic appearance of virions (the infective form of the virus) by electron microscopy, which have a fringe of large, bulbous surface projections creating an image reminiscent of the solar corona or halo. This morphology is created by the viral spike peplomers, which are proteins on the surface of the virus.

The scientific name Coronavirus was accepted as a genus name by the International Committee for the Nomenclature of Viruses (later renamed International Committee on Taxonomy of Viruses) in 1971. As the number of new species increased, the genus was split into four genera, namely *Alphacoronavirus, Betacoronavirus, Deltacoronavirus*, and *Gammacoronavirus* in 2009. The common name coronavirus is used to refer to any member of the subfamily Orthocoronavirinae. As of 2020, 45 species are officially recognised.

History

The earliest reports of a coronavirus infection in animals occurred in the late 1920s, when an acute respiratory infection of domesticated chickens emerged in North America. Arthur Schalk and M. C. Hawn in 1931 made the first detailed report which described a new respiratory infection of chickens in North Dakota. The infection of new-born chicks was characterized by gasping and listlessness with high mortality rates of 40-90%. Leland David Bushnell and Carl Alfred Brandly isolated the virus that caused the infection in 1933. The virus was then known as infectious bronchitis virus (IBV). Charles D. Hudson and Fred Robert Beaudette cultivated the virus for the first time in 1937. The specimen came to be known as the Beaudette strain. In the late 1940s, two more animal coronaviruses, JHM that causes brain disease (murine encephalitis) and mouse hepatitis virus (MHV) that causes hepatitis in mice were discovered. It was not realized at the time that these three different viruses were related.

Human coronaviruses were discovered in the 1960s using two different methods in the United Kingdom and the United States. E. C. Kendall, Malcolm Bynoe, and David Tyrrell working at the Common Cold Unit of the British Medical Research Council collected a unique common cold virus designated B814 in 1961. The virus could not be cultivated using standard techniques which had successfully cultivated rhinoviruses, adenoviruses and other known common cold viruses. In 1965, Tyrrell and Bynoe successfully cultivated the novel virus by serially passing it through organ culture of human embryonic trachea. The new cultivating method was introduced to the lab by Bertil Hoorn. The isolated virus when intranasally inoculated into volunteers caused a cold and was inactivated by ether which indicated it had a lipid envelope. Dorothy Hamre and John Procknow at the University of Chicago isolated a novel cold from medical students in 1962. They isolated and grew the virus in kidney tissue culture, designating it 229E. The novel virus caused a cold in volunteers and, like B814, was inactivated by ether.

Transmission electron micrograph of organ cultured coronavirus OC43 Scottish virologist June Almeida at St. Thomas Hospital in London, collaborating with Tyrrell, compared the structures of IBV, B814 and 229E in 1967. Using electron microscopy the three viruses were shown to be morphologically related by their general shape and distinctive club-like spikes. A research group at the National Institute of Health the same year was able to isolate another member of this new group of viruses using organ culture and named one of the samples OC43 (OC for organ culture). Like B814, 229E, and IBV, the novel cold virus OC43 had distinctive club-like spikes when observed with the electron microscope.

The IBV-like novel cold viruses were soon shown to be also morphologically related to the mouse hepatitis virus. This new group of viruses were named coronaviruses after their distinctive morphological appearance. Human coronavirus 229E and human coronavirus OC43 continued to be studied in subsequent decades. The coronavirus strain B814 was lost. It is not known which present human coronavirus it was. Other human coronaviruses have since been identified, including SARS-CoV in 2003, HCoV NL63 in 2003, HCoV HKU1 in 2004, MERS-CoV in 2013, and SARS-CoV-2 in 2019. There have also been a large number of animal coronaviruses identified since the 1960s.

Microbiology

Structure of a Coronavirus:

Coronaviruses are large, roughly spherical particles with unique surface projections. Their size is highly variable with average diameters of 80 to 120 nm. Extreme sizes are known from 50 to 200 nm in diameter. The total molecular weight is on average 40,000 kDa. They are enclosed in an envelope embedded with a number of protein molecules. The lipid bilayer envelope, membrane proteins, and nucleocapsid protect the virus when it is outside the host cell.

The viral envelope is made up of a lipid bilayer in which the membrane (M), envelope (E) and spike (S) structural proteins are anchored. The molar ratio of E:S:M in the lipid bilayer is approximately 1:20:300. The E and M protein are the structural proteins that combined with the lipid bilayer to shape the viral envelope and maintain its size. S proteins are needed for interaction with the host cells. But human coronavirus NL63 is peculiar in that its M protein has the binding site for the host cell, and not its S protein. The diameter of the envelope is 85 nm. The envelope of the virus in electron micrographs appears as a distinct pair of electron-dense shells (shells that are relatively opaque to the electron beam used to scan the virus particle).

The M protein is the main structural protein of the envelope that provides the overall shape and is a type III membrane protein. It consists of 218 to 263 amino acid residues and forms a layer 7.8 nm thick. It has three domains, a short N-terminal ectodomain, a triple-spanning transmembrane domain, and a C-terminal endodomain. The C-terminal domain forms a matrix-like lattice that adds to the extra-thickness of the envelope. Different species can have either N- or O-linked glycans in their protein amino-terminal domain. The M protein is crucial during the assembly, budding, envelope formation, and pathogenesis stages of the virus lifecycle.

The E proteins are minor structural proteins and highly variable in different species. There are only about 20 copies of the E protein molecule in a coronavirus particle. They are 8.4 to 12 kDa in size and are composed of 76 to 109 amino acids. They are integral proteins (i.e. embedded in the lipid layer) and have two domains namely a transmembrane domain and an extramembrane C-terminal domain. They are almost fully_-helical, with a single-helical transmembrane domain, and form pentameric (five-molecular) ion channels in the lipid bilayer. They are responsible for virion assembly, intracellular trafficking and morphogenesis (budding).

The spikes are the most distinguishing feature of coronaviruses and are responsible for the corona- or halo-like surface. On average a coronavirus particle has 74 surface spikes. Each spike is about 20 nm long and is composed of a trimer of the S protein. The S protein is in turn composed of an S1 and S2 subunit. The homotrimeric S protein is a class I fusion protein which mediates the receptor binding and membrane fusion between the virus and host cell. The S1 subunit forms the head of the spike and has the receptor-binding domain (RBD). The S2 subunit forms the stem which anchors the spike in the viral envelope and on protease activation enables fusion. The two subunits remain noncovalently linked as they are exposed on the viral surface until they attach to the host cell membrane. In a functionally active state, three S1 are attached to two S2 subunits. The subunit complex is split into individual subunits when the virus binds and fuses with the host cell under the action of proteases such as cathepsin family and transmembrane protease serine 2 (TMPRSS2) of the host cell.

After binding of the ACE2 receptor, SARS-CoV spike is activated and cleaved at the S1/S2 level S1 proteins are the most critical components in terms of infection. They are also the most variable components as they are responsible for host cell specificity. They possess two major domains named N-terminal domain (S1-NTD) and C-terminal domain (S1-CTD), both of which serve as the receptor-binding domains. The NTDs recognize and bind sugars on the surface of the host cell. An exception is the MHV NTD that binds to a protein receptor carcinoembryonic antigen-related cell adhesion molecule 1 (CEACAM1). S1-CTDs are responsible for recognizing different protein receptors such as angiotensin-converting enzyme 2 (ACE2), aminopeptidase N (APN), and dipeptidyl peptidase 4 (DPP4).

A subset of coronaviruses (specifically the members of betacoronavirus subgroup A) also has a shorter spike-like surface protein called hemagglutinin esterase (HE). The HE proteins occur as homodimers composed of about 400 amino acid residues and are 40 to 50 kDa in size. They appear as tiny surface projections of 5 to 7 nm long embedded in between the spikes. They help in the attachment to and detachment from the host cell.

Inside the envelope, there is the nucleocapsid, which is formed from multiple copies of the nucleocapsid (N) protein, which are bound to the positive-sense single-stranded RNA genome in a continuous beads-on-a-string type conformation. N protein is a phosphoprotein of 43 to 50 kDa in size, and is divided into three conserved domains. The majority of the protein is made up of domains 1 and 2, which are typically rich in arginines and lysines. Domain 3 has a short carboxy terminal end and has a net negative charge due to excess of acidic over basic amino acid residues.

Genome

SARS-CoV Genome and Proteins:

Coronaviruses contain a positive-sense, single-stranded RNA genome. The genome size for coronaviruses ranges from 26.4 to 31.7 kilobases. The genome size is one of the largest among RNA viruses. The genome has a 5_methylated cap and a 3_polyadenylated tail.

The genome organization for a coronavirus is 5_-leader-UTR-replicase (ORF1ab)-spike (S)-envelope (E)-membrane (M)-nucleocapsid (N)-3_UTR-poly (A) tail. The open reading frames 1a and 1b, which occupy the first two-thirds of the genome, encode the replicase polyprotein (pp1ab). The replicase polyprotein self cleaves to form 16 nonstructural proteins (nsp1-nsp16).

The later reading frames encode the four major structural proteins: spike, envelope, membrane, and nucleocapsid. Interspersed between these reading frames are the reading frames for the accessory proteins. The number of accessory proteins and their function is unique depending on the specific coronavirus.

Replication Cycle

Cell Entry and the Life Cycle of a Coronavirus:

Infection begins when the viral spike protein attaches to its complementary host cell receptor. After attachment, a protease of the host cell cleaves and activates the receptor-attached spike protein. Depending on the host cell protease available, cleavage and activation allows the virus to enter the host cell by endocytosis or direct fusion of the viral envelope with the host membrane.

Genome Translation

On entry into the host cell, the virus particle is uncoated, and its genome enters the cell cytoplasm. The coronavirus RNA genome has a 5_methylated cap and a 3_polyadenylated tail, which allows it to act like a messenger RNA and be directly translated by the host cell's ribosomes. The host ribosomes translate the initial overlapping open reading frames ORF1a and ORF1b of the virus genome into two large overlapping polyproteins, pp1a and pp1ab.

The larger polyprotein pplab is a result of a −1 ribosomal frameshift caused by a slippery sequence (UUUAAAC) and a downstream RNA pseudoknot at the end of open reading frame ORF1a. The ribosomal frameshift allows for the continuous translation of ORF1a followed by ORF1b. The polyproteins have their own proteases, PLpro (nsp3) and 3CLpro (nsp5), which cleave the polyproteins at different specific sites. The cleavage of polyprotein pp1ab yields 16 nonstructural proteins (nsp1 to nsp16). Product proteins include various replication proteins such as RNA-dependent RNA polymerase (nsp12), RNA helicase (nsp13), and exoribonuclease (nsp14).

Replicase-Transcriptase

Replicase-Transcriptase Complex:

A number of the nonstructural proteins coalesce to form a multi-protein replicase-transcriptase complex. The main replicase-transcriptase protein is the RNA-dependent RNA polymerase (RdRp). It is directly involved in the replication and transcription of RNA from an RNA strand. The other nonstructural proteins in the complex assist in the replication and transcription process. The exoribonuclease nonstructural protein, for instance, provides extra fidelity to replication by providing a proofreading function which the RNA-dependent RNA polymerase lacks.

Replication—One of the main functions of the complex is to replicate the viral genome. RdRp directly mediates the synthesis of negative-sense genomic RNA from the positive-sense genomic RNA. This is followed by the replication of positive-sense genomic RNA from the negative-sense genomic RNA.

Transcription of Nested mRNAs and Nested Set of Subgenomic mRNAs:

Transcription—The other important function of the complex is to transcribe the viral genome. RdRp directly mediates the synthesis of negative-sense subgenomic RNA molecules from the positive-sense genomic RNA. This process is followed by the transcription of these negative-sense subgenomic RNA molecules to their corresponding positive-sense mRNAs. The subgenomic mRNAs form a "nested set" which have a common 5'-head and partially duplicate 3'-end.

Recombination—The replicase-transcriptase complex is also capable of genetic recombination when at least two viral genomes are present in the same infected cell. RNA recombination appears to be a major driving force in determining genetic variability within a coronavirus species, the capability of a coronavirus species to jump from one host to another and, infrequently, in determining the emergence of novel coronaviruses. The exact mechanism of recombination in coronaviruses is unclear, but likely involves template switching during genome replication.

Assembly and Release

The replicated positive-sense genomic RNA becomes the genome of the progeny viruses. The mRNAs are gene transcripts of the last third of the virus genome after the initial overlapping reading frame. These mRNAs are translated by the host's ribosomes into the structural proteins and a number of accessory proteins. RNA translation occurs inside the endoplasmic reticulum. The viral structural proteins S, E, and M move along the secretory pathway into the Golgi intermediate compartment. There, the M proteins direct most protein-protein interactions required for assembly of viruses following its binding to the nucleocapsid. Progeny viruses are then released from the host cell by exocytosis through secretory vesicles. Once released the viruses can infect other host cells.

Transmission

Infected carriers are able to shed viruses into the environment. The interaction of the coronavirus spike protein with its complementary cell receptor is central in determining the tissue tropism, infectivity, and species range of the released virus. Coronaviruses mainly target epithelial cells. They are transmitted from one host to another host, depending on the coronavirus species, by either an aerosol, fomite, or fecal-oral route.

Human coronaviruses infect the epithelial cells of the respiratory tract, while animal coronaviruses generally infect the epithelial cells of the digestive tract. SARS coronavirus, for example, infects the human epithelial cells of the lungs via an aerosol route by binding to the angiotensin-converting enzyme 2 (ACE2) receptor. Transmissible gastroenteritis coronavirus (TGEV) infects the pig epithelial cells of the digestive tract via a fecal-oral route by binding to the alanine aminopeptidase (APN) receptor.

Classification

Phylogenetic Tree of Coronaviruses:

Coronaviruses form the subfamily Orthocoronavirinae, which is one of two sub-families in the family Coronaviridae, order Nidovirales, and realm Riboviria. They are divided into the four genera: *Alphacoronavirus, Betacoronavirus, Gammacoronavirus* and *Deltacoronavirus. Alphacoronaviruses* and *betacoronaviruses* infect mammals, while *gammacoronaviruses* and *deltacoronaviruses* primarily infect birds. Genus: *Alphacoronavirus*; type species: *Alphacoronavirus* 1

Species: *Alphacoronavirus* 1 (TGEV, Feline coronavirus, Canine coronavirus), Human coronavirus 229E, Human coronavirus NL63, Miniopterus bat coronavirus 1, Miniopterus bat coronavirus HKU8, Porcine epidemic diarrhea virus, Rhinolophus bat coronavirus HKU2, Scotophilus bat coronavirus 512 Genus *Betacoronavirus*; type species: *Murine coronavirus* (MHV)

Species: *Betacoronavirus* 1 (Bovine Coronavirus, Human coronavirus OC43), Hedgehog coronavirus 1, Human coronavirus HKU1, Middle East respiratory syndrome-related coronavirus, Murine coronavirus, Pipistrellus bat coronavirus HKU5, Rousettus bat coronavirus HKU9, Severe acute respiratory syndrome-related coronavirus (SARS-CoV, SARS-CoV-2), Tylonycteris bat coronavirus HKU4 Genus *Gammacoronavirus*; type species: *Avian coronavirus* (IBV)

Species: *Avian coronavirus*, Beluga whale coronavirus SW1 Genus *Deltacoronavirus*; type species: *Bulbul coronavirus* HKU11 Species: *Bulbul coronavirus* HKU11, Porcine coronavirus HKU15

Origin

Origins of Human Coronaviruses with Possible Intermediate Hosts:

The most recent common ancestor (MRCA) of all coronaviruses is estimated to have existed as recently as 8000 BCE, although some models place the common ancestor as far back as 55 million years or more, implying long term coevolution with bat and avian species. The most recent common ancestor of the *alphacoronavirus* line has been placed at about 2400 BCE, of the *betacoronavirus* line at 3300 BCE, of the *gammacoronavirus* line at 2800 BCE, and of the *deltacoronavirus* line at about 3000 BCE. Bats and birds, as warm-blooded flying vertebrates, are an ideal natural reservoir for the coronavirus gene pool (with bats the reservoir for *alphacoronaviruses* and *betacoronavirus*—and birds the reservoir for *gammacoronaviruses* and *deltacoronaviruses*). The large number and global range of bat and avian species that host viruses has enabled extensive evolution and dissemination of coronaviruses.

Many human coronaviruses have their origin in bats. The human coronavirus NL63 shared a common ancestor with a bat coronavirus (ARCoV.2) between 1190 and 1449 CE. The human coronavirus 229E shared a common ancestor with a bat coronavirus (GhanaGrpl Bt CoV) between 1686 and 1800 CE. More recently, alpaca coronavirus and human coronavirus 229E diverged sometime before 1960. MERS-CoV emerged in humans from bats through the intermediate host of camels. MERS-CoV, although related to several bat coronavirus species, appears to have diverged from these several centuries ago. The most closely related bat coronavirus and SARS-CoV diverged in 1986. The ancestors of SARS-CoV first infected leaf-nose bats of the genus *Hipposideridae*; subsequently, they spread to horseshoe bats in the species *Rhinolophidae*, then to Asian palm civets, and finally to humans.

Unlike other betacoronaviruses, bovine coronavirus of the species *Betacoronavirus* 1 and subgenus *Embecovirus* is thought to have originated in rodents and not in bats. In the 1790s, equine coronavirus diverged from the bovine coronavirus after a cross-species jump. Later in the 1890s, human coronavirus OC43 diverged from bovine coronavirus after another cross-species spillover event. It is speculated that the flu pandemic of 1890 may have been caused by this spillover event, and not by the influenza virus, because of the related timing, neurological symptoms, and unknown causative agent of the pandemic. Besides causing respiratory infections, human coronavirus OC43 is also suspected of playing a role in neurological diseases. In the 1950s, the human coronavirus OC43 began to diverge into its present genotypes. Phylogentically, mouse hepatitis virus (*Murine coronavirus*), which infects the mouse's liver and central nervous system, is related to human coronavirus OC43 and bovine coronavirus. Human coronavirus HKU1, like the aforementioned viruses, also has its origins in rodents.

Infection in Humans

Transmission and Life-Cycle of SARS-CoV-2 Causing COVID-19:

Coronaviruses vary significantly in risk factor. Some can kill more than 30% of those infected, such as MERS-CoV, and some are relatively harmless, such as the common cold. Coronaviruses can cause colds with major symptoms, such as fever, and a sore throat from swollen adenoids. Coronaviruses can cause pneumonia (either direct viral pneumonia or secondary bacterial pneumonia) and bronchitis (either direct viral bronchitis or secondary bacterial bronchitis). The human coronavirus discovered in 2003, SARS-CoV, which causes severe acute respiratory syndrome (SARS), has a unique pathogenesis because it causes both upper and lower respiratory tract infections.

Six species of human coronaviruses are known, with one species subdivided into two different strains, making seven strains of human coronaviruses altogether.

Seasonal distribution of HCoV-NL63 in Germany shows a preferential detection from November to March. Four human coronaviruses produce symptoms that are generally mild, even though it is contended they might have been more aggressive in the past:

Human coronavirus OC43 (HCoV-OC43),_-CoV

Human coronavirus HKU1 (HCoV-HKU1),_-CoV

Human coronavirus 229E (HCoV-229E),_-CoV

Human coronavirus NL63 (HCoV-NL63),_-CoV

Three human coronaviruses produce symptoms that are potentially severe:

Middle East respiratory syndrome-related coronavirus (MERS-CoV),_-CoV

Severe acute respiratory syndrome coronavirus (SARS-CoV),_-CoV

Severe acute respiratory syndrome coronavirus 2 (SARS-CoV-2),_-CoV

Common Cold

Although the common cold is usually caused by rhinoviruses, in about 15% of cases the cause is a coronavirus. The human coronaviruses HCoV-OC43, HCoV-HKU1, HCoV-229E, and HCoV-NL63 continually circulate in the human population in adults and children worldwide and produce the generally mild symptoms of the common cold. The four mild coronaviruses have a seasonal incidence occurring in the winter months in temperate climates. There is no preponderance in any season in tropical climates.

Severe Acute Respiratory Syndrome (SARS)

Characteristics of Zoonotic Coronavirus Strains: MERS-CoV, SARS-CoV, SARS-CoV-2, and related diseases

| | MERS-CoV | SARS-CoV | SARS-CoV-2 |
|---|---|---|---|
| Disease | MERS | SARS | COVID-19 |
| Outbreaks | 2012, 2015, 2018 | 2002-2004 | 2019-2021 pandemic |
| Epidemiology | | | |
| Date of first identified case | June 2012 | November 2002 | December 2019 |
| Location of first identified case | Jeddah, Saudi Arabia | Shunde, China | Wuhan, China |
| Age average | 56 | 44 | 56 |
| Sex ratio (M:F) | 3.3:1 | 0.8:1 | 1.6:1 |
| Confirmed cases | 2494 | 8096 | 126,751,929 |
| Deaths | 858 | 774 | 2,778,310 |
| Case fatality rate | 37% | 9.2% | 2.2% |
| Symptoms | | | |
| Fever | 98% | 99-100% | 87.9% |
| Dry cough | 47% | 29-75% | 67.7% |
| Dyspnea | 72% | 40-42% | 18.6% |

-continued

| | MERS-CoV | SARS-CoV | SARS-CoV-2 |
|---|---|---|---|
| Diarrhea | 26% | 20-25% | 3.7% |
| Sore throat | 21% | 13-25% | 13.9% |
| Ventilatory use | 24.5% | 14-20% | 4.1% |

Notes
a ^ Based on data from Hong Kong.
b ^ Jump up to: _a b Data as of 28 Mar. 2021.
vte In 2003, following the outbreak of severe acute respiratory syndrome (SARS) which had begun the prior year in Asia, and secondary cases elsewhere in the world, the World Health Organization (WHO) issued a press release stating that a novel coronavirus identified by a number of laboratories was the causative agent for SARS. The virus was officially named the SARS coronavirus (SARS-CoV). More than 8,000 people from 29 different countries and territories were infected, and at least 774 died.

Middle East Respiratory Syndrome (MERS)

In September 2012, a new type of coronavirus was identified, initially called Novel Coronavirus 2012, and now officially named Middle East respiratory syndrome coronavirus (MERS-CoV). The World Health Organization issued a global alert soon after.[112] The WHO update on 28 September 2012 said the virus did not seem to pass easily from person to person. However, on 12 May 2013, a case of human-to-human transmission in France was confirmed by the French Ministry of Social Affairs and Health. In addition, cases of human-to-human transmission were reported by the Ministry of Health in Tunisia. Two confirmed cases involved people who seemed to have caught the disease from their late father, who became ill after a visit to Qatar and Saudi Arabia. Despite this, it appears the virus had trouble spreading from human to human, as most individuals who are infected do not transmit the virus. By 30 Oct. 2013, there were 124 cases and 52 deaths in Saudi Arabia.
After the Dutch Erasmus Medical Centre sequenced the virus, the virus was given a new name, Human Coronavirus-Erasmus Medical Centre (HCoV-EMC). The final name for the virus is Middle East respiratory syndrome coronavirus (MERS-CoV). The only U.S. cases (both survived) were recorded in May 2014.
In May 2015, an outbreak of MERS-CoV occurred in the Republic of Korea, when a man who had traveled to the Middle East, visited four hospitals in the Seoul area to treat his illness. This caused one of the largest outbreaks of MERS-CoV outside the Middle East. As of December 2019, 2,468 cases of MERS-CoV infection had been confirmed by laboratory tests, 851 of which were fatal, a mortality rate of approximately 34.5%.

Coronavirus Disease 2019 (COVID-19)

In December 2019, a pneumonia outbreak was reported in Wuhan, China. On 31 December 2019, the outbreak was traced to a novel strain of coronavirus, which was given the interim name 2019-nCoV by the World Health Organization (WHO), later renamed SARS-CoV-2 by the International Committee on Taxonomy of Viruses.
As of 28 Mar. 2021, there have been at least 2,778,310 confirmed deaths and more than 126,751,929 confirmed cases in the COVID-19 pandemic. The Wuhan strain has been identified as a new strain of *Betacoronavirus* from group 2B with approximately 70% genetic similarity to the SARS-CoV. The virus has a 96% similarity to a bat coronavirus, so it is widely suspected to originate from bats as well.

Infection in Animals

Coronaviruses have been recognized as causing pathological conditions in veterinary medicine since the 1930s. They infect a range of animals including swine, cattle, horses, camels, cats, dogs, rodents, birds and bats. The majority of animal related coronaviruses infect the intestinal tract and are transmitted by a fecal-oral route. Significant research efforts have been focused on elucidating the viral pathogenesis of these animal coronaviruses, especially by virologists interested in veterinary and zoonotic diseases.

Farm Animals

Coronaviruses infect domesticated birds. Infectious bronchitis virus (IBV), a type of coronavirus, causes avian infectious bronchitis. The virus is of concern to the poultry industry because of the high mortality from infection, its rapid spread, and its effect on production. The virus affects both meat production and egg production and causes substantial economic loss. In chickens, infectious bronchitis virus targets not only the respiratory tract but also the urogenital tract. The virus can spread to different organs throughout the chicken. The virus is transmitted by aerosol and food contaminated by feces. Different vaccines against IBV exist and have helped to limit the spread of the virus and its variants. Infectious bronchitis virus is one of a number of strains of the species Avian coronavirus. Another strain of avian coronavirus is turkey coronavirus (TCV) which causes enteritis in turkeys.
Coronaviruses also affect other branches of animal husbandry such as pig farming and the cattle raising. Swine acute diarrhea syndrome coronavirus (SADS-CoV), which is related to bat coronavirus HKU2, causes diarrhea in pigs. Porcine epidemic diarrhea virus (PEDV) is a coronavirus that has recently emerged and similarly causes diarrhea in pigs. Transmissible gastroenteritis virus (TGEV), which is a member of the species *Alphacoronavirus* 1, is another coronavirus that causes diarrhea in young pigs. In the cattle industry bovine coronavirus (BCV), which is a member of the species *Betacoronavirus* 1 and related to HCoV-OC43, is responsible for severe profuse enteritis in young calves.

Domestic Pets

Coronaviruses infect domestic pets such as cats, dogs, and ferrets. There are two forms of feline coronavirus which are both members of the species *Alphacoronavirus* 1. Feline enteric coronavirus is a pathogen of minor clinical significance, but spontaneous mutation of this virus can result in feline infectious peritonitis (FIP), a disease with high mortality. There are two different coronaviruses that infect dogs. Canine coronavirus (CCoV), which is a member of the species *Alphacoronavirus* 1, causes mild gastrointestinal disease. Canine respiratory coronavirus (CRCoV), which is a member of the species *Betacoronavirus* 1 and related to HCoV-OC43, cause respiratory disease. Similarly, there are two types of coronavirus that infect ferrets. Ferret enteric coronavirus causes a gastrointestinal syndrome known as epizootic catarrhal enteritis (ECE), and a more lethal systemic version of the virus (like FIP in cats) known as ferret systemic coronavirus (FSC).

Laboratory Animals

Coronaviruses infect laboratory animals, Mouse hepatitis virus (MHV), which is a member of the species *Murine coronavirus*, causes an epidemic murine illness with high mortality, especially among colonies of laboratory mice. Prior to the discovery of SARS-CoV, MHV was the best-studied coronavirus both in vivo and in vitro as well as at the molecular level. Some strains of MHV cause a progressive demyelinating encephalitis in mice which has been used as a murine model for multiple sclerosis. Sialodacryoadenitis virus (SDAV), which is a strain of the species *Murine coronavirus*, is highly infectious coronavirus of laboratory rats, which can be transmitted between individuals by direct contact and indirectly by aerosol. Rabbit enteric coronavirus causes acute gastrointestinal disease and diarrhea in young European rabbits. Mortality rates are high.

Prevention and Treatment

A number of vaccines using different methods have been developed against human coronavirus SARS-CoV-2. Antiviral targets against human coronaviruses have also been identified such as viral proteases, polymerases, and entry proteins. Drugs are in development which target these proteins and the different steps of viral replication. Vaccines are available for animal coronaviruses IBV, TGEV, and Canine CoV, although their effectiveness is limited. In the case of outbreaks of highly contagious animal coronaviruses, such as PEDV, measures such as destruction of entire herds of pigs may be used to prevent transmission to other herds.

End of the Wikipedia information on 2021-03-27.

SUMMARY OF THE INVENTION

The disclosed invention comprises medical therapeutic treatment methods and compositions for a new use of the herb thyme, the new use can also be described as a second medical use since the herb thyme has been previous used to treat various types of viral infections. The herb thyme is also known as Common Thyme or Spanish Thyme. The new use of the herb thyme is for the treatment of the Coronavirus COVID-19 disease and the symptoms of Covid-19 disease, and likely for the prevention of Covid-19 disease. In addition to the new use of the herb thyme, a method of use for the herb thyme for the treatment of COVID-19 disease and its symptoms is also disclosed. The herb thyme and its compounds have previously been shown to have antiviral activity against certain viruses in medical studies.

One such comparative study is antiviral activity against herpes simplex virus type 1 (HSV-1) in vitro as described in a comparative study published in The National Library of Medicine NIH 8600 Rockville Pike Bethesda, MD 20894, PubMed.gov titled "Comparative study on the antiviral activity of selected monoterpenes derived from essential oils" Phytother Res 2010 May;24(5):673-9. doi: 10.1002/ptr.2955.

Another comparative study published by PubMed.gov is titled "Essential Oils for the Treatment of Herpes Simplex Virus Infections" . Chemotherapy 2019;64(1):1-7. doi: 10.1159/000501062. Epub 2019 Jun. 24.

And still another comparative study published by PubMed.gov is titled "Inhibition of herpes simplex virus type 1 by thymol-related monoterpenoids" Planta Med. 2012 October;78(15):1636-8. doi: 10.1055/s-0032-1315208. Epub 2012 Aug. 13.

And yet still another comparative study published by PubMed.gov is titled "Susceptibility of herpes simplex virus type 1 to monoterpenes thymol, carvacrol, p-cymene and essential oils of *Sinapis arvensis* L., *Lallemantia royleana* Benth. and *Pulicaria vulgaris* Gaertn" . 2017 Aug. 30;63(8):42-47. doi: 10.14715/cmb/2017.63.8.10. Cell Mol Biol (Noisy-le-grand)

In addition to the above four studies by The National Library of Medicine NIH PubMed.gov, is an additional study in The Journal of Plant Medicines by Case Adams, PHD, Oct. 3, 2017 (Last Updated On: Apr. 17, 2018) titled "Thyme Antiviral Against Herpes and Other Viruses". The five above disclosed studies mention the antiviral activity and effectiveness of the herb thyme and of certain components of the herb thyme such as thymol in treating certain viral diseases, suggesting the herb thyme and its known antiviral components as being a second use treatment of disease for use in treating the disease Covid-19. Some of the many antiviral substances in the herb thyme may be thymol, camphor, borneol, carvacrol, terpinenes, pinenes, cymene, terpinenols, citral and cineoles, and any one of or combination thereof these constituents may be beneficial for use in the treatment of the disease Covid-19.

DESCRIPTION OF THE INVENTION

The disclosed invention comprises a composition and treatment to prevent the progression and severity of COVID-19 after infection and the occurrence of symptoms of the disease, the treatment is to be initiated soon after the patient develops the first signs of symptoms and preferably initiated within approximately twenty four hours of the onset of symptoms of the disease. The symptoms of the disease comprising but not limited to individually or in combination thereof being fever, headache, sore joints, cough, fatigue, and chills. Generally the fever may be mild or moderate in the initial symptoms stage. The treatment consists of the oral administration of the herb thyme, also know as common thyme (*Thymus Vulgaris*). Generally the leaf of the herb is used and the leaf of the herb is generally ground into powder for easy assimilation by the digestive tract of the patient. Oral administration of the whole non-ground leaf of the herb thyme has not been tested, although, it is conceivable that the whole leaf in an un-ground state of the herb may not digest fully by the patients digestive system and may not achieve the desired results of the treatment. The disclosed treatment is thought to inhibit the replication and activity of the virus allowing the patient to regain normal health and assist in developing immunity to the virus. The disclosed treatment is not known to completely eliminate the coronavirus from the patient therefore resulting in the patient possibly developing the same or similar symptoms of the disease a second or more subsequent times, therefore requiring additional disclosed treatments of the oral administration of the herb thyme.

The herb Thyme in a ground, powdered form and ingested with water in the disclosed treatment method has be shown to reduce and eliminate the symptoms and Covid-19 disease sickness in a single disclosed patient that developed the symptoms of COVID-19 on two different occasions spaced approximately twelve days apart. The disclosed patient recovered from the symptoms each of the two times and was able to return back to his normal working routine within approximately two days. The disclosed patient was treated each time within 24 hours of the onset of the symptoms of the Covid-19 disease.

In the following paragraphs, a description of symptoms and a timeline of symptoms are described from a disclosed patient that has suffered two occurrences of the Covid-19 disease. The disclosed patient was treated using the disclosed herb thyme therapeutic treatment within twenty-four hours after the symptoms started on each occurrences of the Covid-19 disease. The disclosed patient recovered quickly from the symptoms of the disease at each occurrence and now appears to maintain immunity to the disease after approximately fourteen months after the first occurrence of symptoms of the disease.

As described in the medical community, a second set of symptoms have occurred in some patients throughout the world after the patient has suffered an initial set of symptoms of the disease, the second set of symptoms has been described as a re-infection. The term “re-infection” may be an inappropriate description since the virus may remain in the patient’s system for an extended period of time prolonging the infection without symptoms of the infection, and the virus simply may re-activate its aggressive replication process. The second set of symptoms after an initial recovery of the first set of symptoms resulting in an aggressive replication process of the virus may be caused by a number of different and unknown factors, although one factor to possibly cause the virus to re-activate its aggressive replication process may be the ingestion of an substantial amount of sugar and fat such as cane sugar and milk cream in a food such as ice cream, this seemed to be the case as described by the disclosed patient in the following paragraphs of this application. The disclosed patient believes the virus appears to feed off of the sugar and fat to gain strength from the availability of the sugar and fat in the patients system as this scenario seemed to be the scenario that brought on the symptoms of Covid-19 in the disclosed patient symptoms timeline of two occurrences of the Covid-19 disease the disclosed patient suffered from. The first occurrence and first set of symptoms of the disease appeared in the disclosed patient approximately one hour after the ingestion of sugar and milk fat from ice cream and the second occurrence and second set of symptoms of the disease appeared in the disclosed patient approximately one hour after the ingestion of sugar and milk fat from a sweet milk tea drink containing sugar and fat.

The disclosed herb thyme treatment may or may not be effective in reducing the symptoms of an infected patient that has extensive ongoing and severe symptoms of the disease Covid-19 that requires hospitalization or other emergency care. In addition, the safety of the disclosed treatment of Covid-19 using the herb thyme in a severely or moderately infected person is unknown. The side effects of the disclosed treatment seems to be few or none in a healthy patient when the patient is not currently or previous taken prescription drugs when the patient is treated within twenty four hours after the onset of symptoms and wherein the patient is still in basic good health and without breathing difficulties, although this is not substantiated. There appears to be side effects related to orally ingesting of the herb thyme, one of the side effects being elevated blood pressure.

The administration of the disclosed herb thyme treatment in the above mentioned scenario and in the following description of occurrences the disclosed patient has suffered has only been observed on one disclosed patient and has not been observed on patients with severe symptoms that would require hospitalization or other emergency treatments for the disease. Side effects and safety of the disclosed treatment is not known when the disclosed treatment is administered to a patient with moderate or sever symptoms of the disease. In addition, the disclosed patient that has received the disclosed herb thyme treatment in the disclosed limited study was a healthy sixty one year old male with no underlying conditions and has not been prescribed or taking any medications or other drugs. The effect of the disclosed treatment on a patient with underlying conditions or a patient that is currently being treated with prescription or non-prescription drugs is not known. The disclosed patient that was treated with the disclosed thyme herb treatment was suffering from the symptoms of COVID-19, COVID-19 testing at the timeline of March 2020 was not widely available, the disclosed patient was not tested for COVID-19 at that time. The disclosed patient was very likely infected and suffering from COVID-19 with many of the symptoms of Covid-19, but testing verification was not attained. Future testing of the disclosed herbal thyme treatment of COVID-19 on additional patients will verify the effectiveness of the disclosed herbal thyme treatment.

It is possible that a minimal maintenance dose of the disclosed thyme treatment given less often than the disclosed treatment of 0.2 ounces in three oral administrations six to eight hours apart may result in a preventative therapy of the virus to re-activate its aggressive replication process therefore preventing the patient from developing symptoms of the disease. Long term side effects of a maintenance dose of the disclosed treatment of the disease is not known.

One active ingredient of the herb thyme is thymol. Treating a patient with oil of thyme containing thymol may also be a beneficial treatment alternative to using the entire herb in an unaltered but ground into powder state. Additional extractions of the herb thyme may also be a beneficial alternative for oral ingestion for the treatment of Covid-19 instead of oral administration of the entire herb leaf.

A presumed object of the disclosed invention and disclosed method of use seems to be to use the antiviral properties of the herb thyme to depress the activity of the virus reducing the viruses ability to replicate and cause harm to the patient, thus allowing the patient to develop immunity to the virus while the virus is in a depressed state remaining in the patient, although this is just a guess of the effect of the herb thyme on the Covid-19 disease and should not be a determination of fact.

The virus symptoms may resurface in the patient one or more times while the patient is developing immunity to the virus, requiring the patient to then again be treated with the disclosed invention method using the herb thyme utilizing the combination of anti-viral compounds in the herb. If for some reason the patient cannot or does not attain natural immunity to the virus with a reasonable timeframe such as thirty to ninety days, the patient may opt to continue treatment with the disclosed treatment each time the virus affects the patient in a debilitating or symptomatic manner while being diligent and aware of any possible side affects from the ingestion of the herb thyme. One side effect of oral ingesting the herb thyme may be elevated blood pressure. Blood pressure monitoring during the disclosed thyme treatment may be beneficial and a requirement during treatment for safety of the patient. Another side effect of the herb thyme may be that the oral ingestion of the herb may interact with drugs that slow blood clotting.

Using the herb thyme as an effective treatment to COVID-19 may have many advantages to the conventional treatment options described earlier in this application. The herb thyme:

is a natural substance has been known to be possibly safe as described when used as a medicine for short periods of time.

can be easily grown, is currently widely available to the general public, and commonly sold in most grocery stores as a food spice.

may be the most effect substance to use to assist the patient in developing immunity to COVID-19 by simply inhibiting the replication of the virus in the patient allowing the patient to recover sufficiently to develop immunity.

Derivatives of the herb Thyme may also be an effective treatment option for the Covid-19 disease. One such derivative is the thymol. Thymol is found in thyme oil or made synthetically. It may be noted, the disclosed patient was treated with the entirety of the thyme leaf in a ground and powdered state with all of the ingredients of the thyme leaf. Other antiviral derivatives of thyme include, camphor, borneol, carvacrol, terpinenes, pinenes, cymene, terpinenols, citral and cineoles.

Below is a dated timeline of the disclosed patient scenario of symptoms and treatment of the symptoms of the coronavirus COVID-19 two occurrences the patient suffered from.

Tuesday 2020 Feb. 4: The disclosed patient having personal use experience of ingesting thyme and its anti viral properties, ordered four six ounce packs of thyme leaves from Amazon, brand name Yamees.. The thyme order was received by the patient on 2020 Feb. 6. The disclosed patient was aware of the new coronavirus infection going around and made sure he had an additional ample supplies of thyme to fight the infection if he contracted the virus and of the possibility that the virus is deterred by the ingestion of the thyme powder. The disclosed patient promptly ground up one six ounce bag of thyme in the blender to make a rough powder and placed the thyme powder is a sealed jar and placed the jar in the refrigerator. On or near 2020 Feb. 6 the disclosed patient also purchased a 1.38 ounce can of thyme powder from Fry's food store in the Kroger brand.

Thursday 2020 Feb. 6: The disclosed patient received his order of thyme from Amazon.

Monday 2020 Feb. 24: The disclosed patient purchased 2 lbs. of hulled sunflower seeds at Winco at 59$^{th}$ Ave & Bell Rd. in Glendale AZ for about $1.39 lb.

Monday 2020 Feb. 24: The disclosed patient ate about 2 ounces of the sunflower seeds. The sunflower seeds tasted rancid with bad taste. The disclosed patient threw the portion of the sunflower seeds he did not eat in the trash. The disclosed patient is assuming that the sunflower seeds were from China for the fact they only cost $1.39 per lb.

Monday 2020 Feb. 24 through Sunday 2020 Mar. 1 till 7 pm: The disclosed patient felt fine without any noticeable health problems. The disclosed patient worked in Camp Verde AZ on a small farm he owns on Saturday and Sunday Feb. 20, 2020 and Mar. 1, 2020.

Sunday 2020 Mar. 1 7:30 pm: The disclosed patient returned from the grocery store (Bashes) in Camp Verde at about 7:30 pm and the disclosed patient ate 1 pint of natural ice cream that had a high content of sugar and milk cream. The ice crème was Haagen Dazs pineapple coconut. The ingredients were Cream, skim milk, cane sugar, pineapple, egg yolks, natural flavor (contains coconut), rum.

Sunday 2020 Mar. 1 8:00 pm: Soon after and with thirty to sixty minutes after eating the ice cream the disclosed patient developed a slight fever and a slight headache with chills and aching in his bones. That night the disclosed patient testing the soreness in his joints, tried to do a couple of pushups, the disclosed patient could not do any pushups because of soreness in the shoulders, the shoulders are sore, the disclosed patients shoulders are not normally sore when doing pushups. The disclosed patient's headache and fever persisted through out the night.

Monday 2020 Mar. 2 5:00 am: The disclosed patient is still felling sick but not knowing what the problem is, the disclosed patient decided he could not safely drive back to Phoenix in the morning darkness. The disclosed patient decided to go to the local restaurant in Camp Verde AZ called the Verde Café and eat breakfast before driving back to Phoenix during daylight hours.

Monday 2020 Mar. 2 6:00 am to 7:00 am: The disclosed patient arrived at the restaurant and sat down and ordered breakfast. The disclosed patient ate the usual 2 eggs, hash browns, toast and coffee for the headache. The disclosed patient did not realize what his sickness could have been, nor did the patient communicate to any of the two or three other people sitting at the same table as the disclosed patient that the disclosed patient was not feeling well. The disclosed patient did notice that while sitting in the restaurant he was getting sharp pains in his lower back in the kidney area, felt like being stabbed in the lower back and a little to the side.

Monday 2020 Mar. 2 9:30 am: The disclosed patient arrives in Phoenix and the disclosed patient still not feeling well with a slight fever and headache. The disclosed patient's single employee Brian says he is finished with the current job schedule and ready to meet with the disclosed patient at the next job at 51$^{st}$ Ave & McDowell Rd where Brian and the disclosed patient need to complete some electrical circuit trouble shooting. Brian and the disclosed patient meet and finished the trouble-shooting job by noon, the disclosed patient did not feel well during the work, but the job needed to be completed as it was behind schedule. The disclosed patient spent the rest of the day at home resting.

Monday 2020 Mar. 2 10:30 am: A former employee Jeff is in town from Wisconsin and sent the patient a text to see if the disclosed patient is in Phoenix. Jeff requested the disclosed patient help him grease the front end of his truck as it is making noise. The disclosed patient told him sure, be glad to. The disclosed patient still was not feeling good, still did not know why or have any inclination he had contracted the coronavirus Covid-19.

Monday 2020 Mar. 2 2:10 pm: Although the disclosed patient is still not feeling well and has no clue to what his sickness is Monday 2020 Mar. 2 3:00 pm: Still feeling bad with the persistent slight headache and persistent slight fever, the disclosed patient is now assuming he has Covid-19 disease and decided to start therapeutic treatment for himself with the herb thyme. For this first dose, the disclosed patient used the bulk Thyme he purchased from Amazon that he had previously ground up to a rough powder in his blender. The disclosed patient added one heaping teaspoon (approximately 0.2 oz) into a full glass of water and let the thyme sit in the water for about ½ hour until the thyme was soaked down with water. The disclosed patient then proceeded to drink the entire glass of water containing the thyme. The disclosed patient had a small meal that day at El Pollo Loco at 51$^{st}$ ave and McDowell Rd at about 11:00 am.

Monday 2020 Mar. 2 8:00 pm: The disclosed patient is stilling felling sick with the persistent slight headache, slight fever and body aches. The disclosed patient decided to ingest another heaping teaspoon dose of thyme with water in the same manner as earlier except this time the patient used the thyme powder in a small can he bought at the Fry's grocery store. The disclosed patient used one heaping teaspoon (approximately 0.2 oz) again and let the thyme powder sit in the water before ingesting. The disclosed patient had mostly an empty stomach when the thyme was ingested. The disclosed patient is still feeling sick. The disclosed patient went to sleep. Prior to going to sleep, The disclosed patient was thinking to himself that this sickness is nothing like I have ever felt before, the headache at the same time as the slight fever and tremendous joint pain was foreign to him even though the disclosed patient has previously had the seasonal flu in years past, although the disclosed patient has also treated the seasonal flu in the years past with the herb thyme and therefore he has not previously suffered to any large degree from the seasonal flu.

Tuesday 2020 Mar. 3 4:30 am: The disclosed patient woke up after a night of sleep where he did not sleep well. The headache had bothered the disclosed patient all night and prevented him from sleeping well. The fever was still with the disclosed patient, but the headache bothered him more than the fever. The disclosed patient phone called the schedule to his employee Brian to keep him busy most of the day.

Tuesday 2020 Mar. 3 5:30 am: The disclosed patient is still feeling bad, the disclosed patient decided to ingest another heaping teaspoon dose of thyme using the thyme powder in a small can he bought at the grocery store. The disclosed patient ingested the thyme and water on an empty stomach.

Tuesday 2020 Mar. 3 8:30 am: The disclosed patient started to feel much better, the headache is reduced and the slight fever seems to be almost gone. The disclosed patient placed a automotive grease gun with grease in his truck expecting to meet with Jeff and grease his trucks front end. The disclosed patient went out for a cup of coffee at $28^{th}$ Ave & Bell rd at The Gourmet Bagel coffee shop arriving at about 9:00 am. The disclosed patient sent a text to Jeff saying that he can grease his truck right now if he is available, but the disclosed patient told Jeff he is feeling a little under the weather and probably should not meet with his family incase he is contagious, Jeff responded Ok and met the patient about 20 minutes later at the coffee shop. The disclosed patient greased the zerk fittings on Jeff s truck and then the disclosed patient and Jeff talked old times for about 20 minutes in the parking lot located to the west side of the Fry's grocery store in the same vicinity of the coffee shop.

Tuesday 2020 Mar. 3 11:00: The disclosed patient received a text from his employee, Brian saying he is finished with the job schedule and would like to meet up at the storage at $43^{rd}$ & Peoria to install the new truck door handle the patient bought for the bucket truck. The disclosed patient and Brian met at about noon and installed the door handle, it took about 2 hours complete and was a difficult job. The disclosed patient was feeling better by now and working on the truck door handle was not a great problem even though he was still a little weak. The disclosed patient gave Brian his schedule for Wednesday morning to first thing go to the large centers in Surprise the company services.

Wednesday 2020 Mar. 4 5:30 am: The disclosed patient is feeling pretty good, he texted Brian that he will meet him in Surprise. The disclosed patient arrived in Surprise and worked a few hours with Brian on the centers changing light bulbs and ballasts. The disclosed patient was feeling almost back to normal Friday 2020 Mar. 6 9:20 am: The disclosed patient is feeling fine again and pretty much back to normal except for a little weakness.

Friday 2020 Mar. 6 through Wednesday Mar. 11, 2020: The patient is feeling pretty good and out in the field working with Brian, all seems normal.

Thursday 2020 Mar. 12 6:00 am through 1:00 pm: The disclosed patient worked with Brian in the field most of the day and he worked fine. The last stop of the day was at Litchfield Rd and Van Buren street in Avondale. At about 1:00 pm the patient left to allow Brian to finish the job while the disclosed patient went across the street for a cup of coffee to do some paperwork and to check the phone emails. The disclosed patient ordered a coffee but the server said the coffee is real strong using six shots of espresso, so the disclosed patient opted for a tea instead. The server said the tea is a milk tea and the disclosed patient said OK. The disclosed patient drank the tea and the tea was real sweet, too sweet for the disclosed patient's taste.

Thursday 2020 Mar. 12 5:00 pm: A few hours after drinking the very sweet milk tea, the disclosed patient started to get a headache and a slight fever with sore joints very similar to the same feeling he had on Sunday Mar. 1, 2020 8:00 pm after eating the sweet ice cream. This time, the disclosed patient says the sickness felt a little bit worse than the Mar. 1, 2020 sickness. The disclosed patient gave himself a dose of the thyme at about 8:00 pm using the thyme he ground in his blender just like previously and then went to sleep.

Friday 2020 Mar. 13: The disclosed patient was pretty much sick all day with a slight fever and a little more than a slight headache. The disclosed patient did not do too much all day, but he did give himself two more doses of the thyme from the can of thyme purchased from the grocery store, each dose spaced out during the day about 8 hours apart.

Saturday 2020 Mar. 14: The disclosed patient still felt a little sick on Saturday. The disclosed patient rested most of the day but was able to weed eat the grass at his house in Phoenix with a weed eater later in the afternoon. The disclosed patient starting to feel better Saturday evening, but not yet completely better.

Sunday 2020 Mar. 15: The disclosed patient is feeling better today, he left to travel up north to Camp Verde at about 11:00 am and arriving in camp Verde about 12:30 pm. The ground is too wet on the property from rain to work on the property. The disclosed patient completed some paperwork in his trailer for the rest of the day. The disclosed patient stayed the night in Camp Verde, the disclosed patient felt fine.

Monday 2020 Mar. 16 4:30 am: The disclosed patient is feeling good today, he drove into Phoenix early in the morning and met Brian on the job at $64^{th}$ street and Greenway road to help him work on a monument sign.

Monday 2020 Mar. 23 4:00 pm: The disclosed patient ate 6 Valencia oranges that are organic and picked from his backyard orange tree. The disclosed patient experiences no ill effects from eating the high sugar oranges the same day and in the days after eating the oranges.

Monday 2020 Mar. 31 6:00 pm: The disclosed patient again ate 6 Valencia oranges for a third time within four days. The disclosed patient experiences no ill effects from eating the high sugar oranges the same day and in the following days.

Thursday 2020 Mar. 26 6:00 pm: The disclosed patient again ate 7 Valencia oranges for a second time within nine days. The disclosed patient experiences no ill effects from eating the high sugar oranges the same day and in the following days. The disclosed patient experiences no ill effects from eating the high sugar oranges the same day and in the following days.

Thursday 2020 Apr. 2 7:00 am: The disclosed patient ate two high sugar and high fat donuts bought at Bosa Donuts at 75th ave and Cactus rd in Glendale AZ. One donut was a strawberry and cheese croissant and the other donut was an apple-sugar filled donut. The disclosed patient experienced no ill effects from eating the high sugar donuts the same day. The disclosed patient performed labor the same day at the same location as the Bosa Donuts from 7:15 amp to 1:40 pm as he and his employee Brian provided electrical circuits to a monument sign on the same property. The work consisted of medium to hard labor digging a trench and installing underground heavy metal conduit and then covering the conduit with excavated dirt, then proceeding to install the electrical circuits.

Wednesday 2020 Jul. 8 2:17 pm: The disclosed patient has not had a recurrence of Covid-19 symptoms since Mar. 3, 2020 and Mar. 14, 2020. The disclosed patient appears to have developed immunity to covid-19 disease. The disclosed patient has eaten all types of food including fat and sugar. The disclosed patient has very rarely worn a facial mask except when in a large group of people like a grocery store when required by the State of Arizona and the City of Phoenix. The disclosed patient does not wear a mask while at work. The disclosed patient has not ingested any thyme powder or any type of thyme since Mar. 13, 2020 and has not experienced any Covid-19 symptoms up to the present of March 31, 2021. The disclosed patient believes he has immunity and will not develop symptoms to the Covid-19 disease in the future for at least two years.

The sickness the disclosed patient had on 2020 Mar. 1 and on 2020 Mar. 12 appeared to feel the same to the disclosed patient like it was the same sickness. The disclosed patient says it seems as though the virus stayed in his system after the first bout of symptoms on 2020 Mar. 1, the thyme treatment seems to have weakened the virus. On 2020 Mar. 1 the disclosed patient was fine until he ate the very sweet ice cream that was loaded with cane sugar. The disclosed patient's fever came on about twenty to sixty minutes after eating the ice cream.

Then again on 2020 Mar. 12 after the patient ingested a large amount of sugar from milk tea, he experienced very similar symptoms he had on 2020 Mar. 1. The disclosed patient says it appears the virus was still alive in his system just waiting to be fed a good amount of sugar to start aggressive replication and affecting his body again.

The disclosed patient feels that the thyme does not kill the virus, but that the thyme inhibits the virus enough to allow the body to attack the virus with the body's immune system. The disclosed patient says it appears three heaping teaspoon doses of the thyme mixed with water and each dose of one heaping teaspoon of thyme powder taken about 8 hours apart is enough to inhibit the virus to get the desired result of recovery started. The disclosed patient also feels it also appears that sugar and fat feeds the virus and increases its replication intervals and severity of the symptoms.

The disclosed patient feels that a minimal single dose of approximately ⅛ of a heaping teaspoon of thyme powder everyday ingested in the previous stated method will act as a deterrent to symptoms flaring up after a patient has been infected and recovered from Covid-19. The disclosed patient feels that ingesting thyme leaves soaked in water that are not ground up into powder may not duplicate the favorable effects of the treatment the disclosed patient experienced when he treated the coronavirus infection with thyme powder soaked in water. The disclosed treatment for COVID-19 is the oral ingestion of the herb thyme in a ground, powdered form and soaked in a liquid such as water for about thirty minutes and then ingested with the liquid. Six to ten ounces of water may be used to soak the thyme in and the water is to be drank with the ingestion of the thyme. The treatment is meant for a patient that has an onset of symptoms such as symptoms comprising but not limited to individually or in combination thereof fever, headache, sore joints, cough, fatigue, chills usually with the last one to three days. The disclosed patient initial infection of the virus seems to be between five to ten days prior to the onset of symptoms if the disclosed patient is right about being infected with the coronavirus form the sunflower seeds he ingested.

The method for treatment for a dose is to add approximately one heaping teaspoon (approximately 0.2 ounces) of ground, powdered Thyme to a six to ten ounces of water in a glass residing in a room temperature (approximately 70 degrees F.) environment. Before drinking the water and the Thyme mixture, the water and thyme powder should sit idly for about thirty minutes to allow the water to soak fully into the Thyme powder, hydrating the Thyme powder fully and allowing the mixture to be stirred with the Thyme powder dispersing the Thyme powder into the water without any dry Thyme powder residing on top of the water surface.

The patient should then drink the first dose of water and Thyme powder within a one half hour timeframe. A second dose of Thyme powder and water should be orally ingested about six to eight hours after the first dose. A third dose of thyme and water should be orally ingested about six to eight hours after the second dose. The patient should rest or sleep if possible through out the dosing process. The patient may not feel any relief from the COVID-19 symptoms until after the third dose of the thyme powder and water, and any relief may take three to six hours after the third dose depending on the severity of the infection. In the time between the first dose and the third dose oft the thyme powder, it may be beneficial for the patient to refrain from eating food or just eat very light food during this time.

The single disclosed patient in the study felt relief approximately three hours after the third dose of the thyme powder and water. If a patient does not feel relief from the symptoms within eight hours after the third dose of thyme powder and water, a fourth dose may be considered depending on the patients condition or possible side effects of the thyme powder and water mixture. The patient should also keep in mind any possible side effects that may occur with the thyme powder and water interacting with prescription or non-prescription drugs, especially blood thinners.

One object of this disclosed invention is for the patient to develop and gain immunity to allow his or her immune system to fight and contain the replication of the virus, therefore preventing symptoms to appear in the patient when the patient harbors the virus. The preferred method in the disclosed invention of gaining immunity to the virus is for the patient to participate in a regime of oral ingestion of thyme and water in three or more doses. The patient may require one or more regimes or oral ingestion of the thyme and water if the symptoms of the disease reappear after the first regime. Each regime will be ingested intermittently with a period of time between each regime to allow the patients immune system to perform the work of fighting the virus when the virus is in a weakened state. The period of time between each regime is usually in the range of one week to four weeks depending on the patient and the patients health and diet and when or if the symptoms reappear, the intake of sugar should be restricted during the immunity building time period so as to not feed the virus a preferred nutrient of the virus. The number of regimes needed for the patient to build immunity against the virus will also depend on the patents health, age and diet. The possibility exists that some patients will not be able to develop sufficient immunity to fight off symptoms of the viral infection and may need to ingest the thyme and water on a regular basis or seek additional medical treatment of a different type. The single patient in the disclosed study required a second regime of thyme and water approximately two weeks after the first regime. The second set of symptoms appearing soon after the patient ingested a large amount of sugar and fat in a milk tea drink. The second set of symptoms reappeared within two hours after the sugar infused tea drink was ingested. As of the date of this writing (2021 Mar. 31), it has been one year since the onset of the second set of symptoms with no re-occurrence of symptoms a third time even though the patient has ingested a moderate amount of sugar and fat by eating donuts, ice cream and oranges, the oranges being of the Valencia variety known for a high sugar content. It appears the patient has developed immunity or at least partial immunity to the virus, additional time will tell in the months ahead.

The testing of a single patient is preliminary and further testing needs to be accomplished to verify the effectiveness and safety of the disclosed treatment for all different types of patients with different medical conditions or deficiencies. This treatment method using thyme and water was successful on only one patient and is not medical advice for any individual.

Extracted components of the herb thyme either singularly, mixed with other extracted components of the herb or mixed with the entire leaf of the herb may be very effective in the treatment of Covid-19 disease. A composition comprising of i) the whole leaf of the herb thyme, or ii) one or more extracted components of the whole leaf of the herb thyme, or iii) a mixture of the whole leaf of the herb thyme combined with one or more extracted components of the whole leaf of the herb thyme for oral ingestion should be the basis for the treatment or the prevention of the disease Covid-19. The herb thyme may be more effective in a ground state instead of a whole state in the treatment of Covid-19. The herb in the ground state may allow the herb to digest more effectively in the digestive system of the patient. In addition, the method of combining the ground state of the herb or the whole thyme leaf with a liquid such as water may also improve the effectiveness of the digestion system in digesting the herb. Another alternative may be for the herb thyme to be combined with food for the prevention or treatment of the disease Covid-19. Synthetic thymol may also be an alternative to the natural form of thymol form the herb thyme when used as an active ingredient for the treatment or prevention of Covid-19 disease.

A broad method for using the composition of claim 1 for use in the treatment of the disease Covid-19 disease in a patient experiencing the beginning stages of the symptoms of the disease, the treatment beginning within approximately twenty-four hours after the onset of COVID-19 symptoms that may comprise of but are not limited to individually or limited to in combination thereof; fever, headache, sore joints, cough, fatigue, and chills, the method of use comprising the steps of:

a) orally ingesting a first dose of the herb thyme,
b) orally ingesting a second dose of the herb thyme within approximately six to eight hours after the first dose of the herb thyme, and
c) orally ingesting a third dose of the herb thyme within approximately six to eight hours after the second dose of the herb thyme.

A detailed method for using the herb thyme for use in the treatment of COVID-19 disease in a patient experiencing the beginning stages of the symptoms of the disease, the treatment beginning within approximately twenty-four hours after the onset of COVID-19 symptoms that may comprise of but are not limited to individually or limited to in combination thereof; fever, headache, sore joints, cough, fatigue, and chills, the method of use comprising the steps of:

a) the patient staying hydrated with water throughout the entire treatment duration,
b) creating a test dose of the herb thyme in a ground state of thyme and water to prepare for oral ingestion of the test dose of the thyme powder and the water, the test dose is to determine if the patient has an abnormal or dangerous reaction to the ingestion of a larger dose of the thyme powder and the water, the abnormal or dangerous reaction may consist of a blood pressure or pulse increase in the patient that might be considered to be dangerous to the patients health, creating the test dose of the thyme powder and water comprising the steps of:
   i) placing a quarter teaspoon of approximately 0.05 ounces of powdered thyme in six to twelve ounces of water in an environment of air temperature at about seventy degrees Fahrenheit, the water temperature also being about seventy degrees Fahrenheit in temperature,
   ii) the thyme powder will generally initially float on the surface of the water, and
   iii) allowing the thyme to set in the water for thirty minutes or until the water has fully saturated the thyme powder allowing the thyme powder to be stirred and mixed into the water without any dry thyme powder remaining floating on the surface of the water,
c) prior to orally ingesting the test dose of the thyme powder and water, the patient is monitored by taking and recording the vital signs of the patient including but not limited to: the pulse rate, the body temperature, and the blood pressure, all vital signs taken and recorded while the patient is resting,
d) the patient orally ingests the test dose of the thyme powder and water, the entirety of the thyme powder and water being orally ingested within a thirty minute timeframe,
e) the patient being monitored for at least one hour after orally ingesting the test dose, the monitoring of the patient includes recording the vital signs of the patient including but not limited to; the pulse rate, the body temperature, and the blood pressure while resting,
f) if the patient does not have an abnormal or dangerous reaction to the test dose such as a blood pressure or a pulse rate increase in the patient that might be considered to be dangerous to the patients health, the patient will immediately orally ingest a first dose of the thyme power and water after creating the first dose of the thyme powder and water,
g) the patient or patients assistant creates a first dose of powdered thyme and water to prepare for oral ingestion of the thyme powder and the water, creating the first dose of the thyme powder and water comprising the steps of:
   i) placing a heaping teaspoon of approximately 0.2 ounces of ground powdered thyme in six to twelve ounces of water in an environment of air temperature at about seventy degrees Fahrenheit, the water temperature also being about seventy degrees Fahrenheit in temperature,
   ii) the thyme powder will generally float on the surface of the water, and iii) allowing the thyme to set in the water for thirty minutes or until the water has fully saturated the thyme powder allowing the thyme powder to be stirred and mixed into the water without any dry thyme powder remaining on the surface of the water, h) the patient ingests the first dose of the thyme powder and water, i) the patient is monitored for at least one hour after orally ingesting the first dose of thyme powder and water, the monitoring of the patient includes periodically recording the vital signs of the patient including but not limited to; the pulse rate, the body temperature, and the blood pressure while resting, j) if the patient does not have an abnormal or dangerous reaction to the first dose such as a blood pressure or pulse increase in the patient that might be considered to be dangerous to the patients health, the patient will rest for six to eight hours until taking a second dose of the thyme powder and water. If the patient has an abnormal or dangerous reaction to the first dose, the patient seeks medical attention, k) six to eight hours after the first dose of thyme powder and water was orally ingested by the patient, the patient or the patient's assistant creates a second dose of the powdered thyme and water in the same manner the first dose was created, and the patent orally ingests the second dose of the thyme powder and water in the same manner as the first dose, preferably refraining from food and sugars between the first dose and second dose of the thyme powder and water, l) the patient is monitored for at least one hour after orally ingesting the second dose of thyme powder and water, the monitoring of the patient includes periodically recording the vital signs of the patient including but not limited to; the pulse rate, the body temperature, and the blood pressure while resting, m) if the patient does not have an abnormal or dangerous reaction to the second dose such as a blood pressure or pulse increase in the patient that might be considered to be dangerous to the patients health, the patient will rest for six to eight hours until taking a third dose of the thyme powder and water. If the patient has an abnormal or dangerous reaction to the second dose, the patient seeks medical attention, n) six to eight hours after the second dose of thyme powder and water was ingested by the patient, the patient or the patient's assistant creates a third dose of the powdered thyme and water in the same manner the first and the second dose was created, and the patient orally ingests the third dose of the thyme powder and water in the same manner as the first dose and the second dose was orally ingested, preferably refraining from food and sugars between the second dose and third dose of the thyme powder and water, o) the patient preferably refrains from food and sugars for four to six hours after the third dose of the powdered thyme and water, p) the patient is monitored for at least one hour after orally ingesting the second dose of thyme powder and water, the monitoring of the patient includes periodically recording the vital signs of the patient including but not limited to; the pulse rate, the body temperature, and the blood pressure while resting. If the patient has an abnormal or dangerous reaction to the third dose, the patient seeks medical attention, q) the patient stays hydrated prior to the first dose of thyme powder and after the third dose of thyme powder and water, r) eight hours after the third dose of the thyme powder and water, the patient is again monitored for improvement of symptoms of the disease, if the symptoms of the disease do not improve, the patient should seek additional medical care from a health care provider, and the dosage quantities are formulated for a healthy one hundred and seventy pound male 62 years of age with no pre-existing medical conditions such and high blood pressure or diabetes, the dosage formulations may need to be adjusted for a younger or older person that is either lighter in weight or heavier in weight, monitoring of the patient by a health care professional is strongly recommended and may be necessary for the safety of the patient.

Alternative methods of orally ingesting the herb thyme or its active ingredients may be in other forms such as a pill or a capsule. A pill or capsule form may be a much more pleasant way of ingesting the herb thyme since the herb in a powder state and mixed with a liquid such as water can be a very bitter solution to ingest and may be repugnant to some people. The effectiveness of a pill or a capsule form in treating the disease Covid-19 may be diminished if complete digestion is not attained. In addition stomach or intestinal irritation may develop in some forms of ingestion of the herb.

I claim:

1. A method for a therapeutic treatment of a coronavirus disease Covid-19 in humans, the method comprises oral ingestion of an herb thyme used in a therapeutically effective dose or dosage regime.

2. The method of claim 1 wherein the herb thyme comprises whole thyme leaf.

3. The method of claim 1 wherein the herb thyme affects or interferes with a mechanism of the coronavirus, the affected or interfered mechanism is a special surface glycoprotein called a "spike", the herb thyme inhibiting the activity of the coronavirus.

4. The method of claim 2 wherein the whole thyme leaf affects or interferes with a mechanism of the coronavirus, the affected or interfered mechanism is a special surface glycoprotein called a "spike", the whole thyme leaf inhibiting the activity of the coronavirus.

5. The method of claim 1, or claim 2, wherein the dosage regime comprises at least a first dose, a second dose, and a third dose.

6. The method of claim 5 wherein the second dose is ingested approximately six to eight hours after the first dose, and the third dose is ingested approximately six to eight hours after the second dose.

7. The method of claim 6 wherein the treatment dosage regime begins with taking the first dose within twenty-four hours after an onset of symptoms of the disease.

8. The method of claim 6 comprising a fourth or more doses; the fourth or more dose being ingested approximately six to eight hours after the previous dose is ingested.

9. The method of claim 1 wherein the herb thyme is in a dried state.

10. The method of claim 2 wherein the whole thyme leaf is in a dried state.

11. The method of claim 1 wherein the herb thyme is formed into a pill or enclosed in a capsule.

12. The method of claim 2 wherein the whole thyme leaf is formed into a pill or enclosed in a capsule.

13. The method of claim 1 additionally comprising an extracted component or a combination of extracted components of the herb thyme in addition to an entirety of ingredients of the herb thyme.

14. The method of claim 2 additionally comprising an extracted component or a combination of extracted components of the whole thyme leaf in addition to an entirety of ingredients of the whole thyme leaf.

15. The method of claim 13 or claim 14 wherein the extracted component or the extracted components comprises one or more of: thymol, camphor, borneol, carvacrol, terpinenes, pinenes, cymene, terpinenols, citral and cineoles, or any combination thereof.

* * * * *